United States Patent [19]

Jennings et al.

[11] 4,138,428

[45] Feb. 6, 1979

[54] DIMERIZATION PROCESS

[75] Inventors: James R. Jennings; Philip J. Hogan; Lawrence F. M. Kelly, all of Runcorn, England

[73] Assignee: Imperial Chemical Industries Limited, London, England

[21] Appl. No.: 841,924

[22] Filed: Oct. 13, 1977

[30] Foreign Application Priority Data

Oct. 21, 1976 [GB] United Kingdom ............... 45324/76
Oct. 21, 1976 [GB] United Kingdom ............... 52888/76
Apr. 12, 1977 [GB] United Kingdom ............... 15029/77

[51] Int. Cl.$^2$ .................... C07C 121/20; C07C 120/00
[52] U.S. Cl. .............................. 260/465.8 D; 260/945; 260/951; 260/962
[58] Field of Search ................................. 260/465.8 D

[56] References Cited

U.S. PATENT DOCUMENTS 3,574,702   4/1971   Feldman et al. ............. 260/456.8 D

FOREIGN PATENT DOCUMENTS 1268614   5/1968   Fed. Rep. of Germany.
1293155   4/1969   Fed. Rep. of Germany.
2120977  11/1971   Fed. Rep. of Germany.
1499708   9/1967   France.
1154275   6/1969   United Kingdom ............. 260/465.8 D
1177182   1/1970   United Kingdom ............. 260/465.8 D

OTHER PUBLICATIONS

Clark et al., Quarterly Reviews, 18 (1964), pp. 295–320.
Organo–Phosphorus Compounds, Kosalapoff et al., (1972), pp. 266, 268, 470, 471, John Wiley & Sons.

*Primary Examiner*—Joseph Paul Brust
*Attorney, Agent, or Firm*—Cushman, Darby & Cushman

[57] ABSTRACT

Process for the dimerization of acrylonitrile to predominantly straight-chain 1,4-dicyanobutenes (DCB). The ACN is contacted with an organic phosphinite or phosphonite having at least one substituted aryl group attached to the phosphorus atom in the presence of an inert proton-donating solvent and, optionally, an inert non-hydroxylic cosolvent preferably a hydrocarbon, the ACN and solvent(s) being substantially dry. Selectivities of 95% or even 98%, with respect to 1,4 - DCN, may be obtained.

9 Claims, No Drawings

DIMERIZATION PROCESS

This invention relates to a dimerisation process and, especially, to a process for the dimerisation of acrylonitrile to linear $C_6$ dinitriles.

In our co-pending British Patent Application Nos. 45324/75 and 52888/75 we describe and claim a process for the dimerisation of acrylonitrile to predominantly straight-chain $C_6$ dimers comprising contacting the acrylonitrile with an organic phosphorus (III) compound which has at least one hydrocarbyl and at least one alkoxy or cycloalkoxy group attached to the phosphorus atom or atoms, the acrylonitrile being dissolved in an organic solvent capable of donating protons and the acrylonitrile and solvent being substantially dry.

We have now found that when at least one of the hydrocarbyl groups is selected from certain substituted aromatic groups, the rate of dimer formation is considerably enhanced.

According to the present invention, a process for the dimerisation of acrylonitrile to predominantly straight-chain $C_6$ dimers comprises contacting the acrylonitrile with an organic phosphorus (III) compound, the acrylonitrile being dissolved in an organic solvent capable of donating protons but substantially unreactive with acrylonitrile and the phosphorus (III) compound under the dimerisation conditions, the acrylonitrile and solvent being substantially dry, and the phosphorus (III) compound being one of formula:

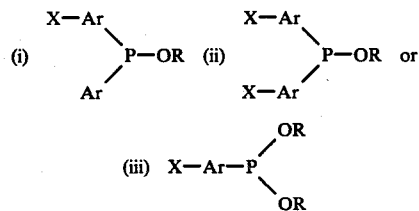

where Ar is an aromatic nucleus, e.g. phenyl or naphthyl, and where groups X, which may be the same or different, are electron donating substituents of the aromatic nucleus which give rise to a negative Hammett $\sigma$ constant; and R represents an alkyl or cycloalkyl group. Substituents X may be in the para or meta positions; but are preferably para. In the case of compounds of formula (ii) above, substituents X may be para in one Ar group but meta in the other.

It will be appreciated that the phosphorus (III) compounds defined above are either phosphinites or phosphonites.

A discussion on Hammett $\sigma$ constants and a table showing values for most common substituents is to be found in an article by Clark and Perrin in Quarterly Reviews, Vol 18, 1964 pp 295-320.

Examples of suitable substituents X include alkoxy groups, e.g. methoxy, ethoxy, i-propoxy and t-butoxy; alkyl groups, e.g. methyl, ethyl and propyl; and alkyl amino groups, e.g. dimethylamino and diethylamino. The alkoxy, alkyl and alkylamino groups preferably contain from 1 to 8 carbon atoms. It is essential that group X should be one which does not react adversely with the components of the reaction system.

Suitable groups R include alkyl groups such as methyl, ethyl, isopropyl, neopentyl, 2-ethylhexyl; and cycloalkyl groups such as cyclohexyl. It is noted that bulky groups R, for example isopropyl, may give rise to increased catalyst lifetime.

The presence of an organic solvent is essential to our process, since in the absence of solvent rapid polymerisation of the acrylonitrile occurs. Suitable solvents are proton-donating solvents which are substantially unreactive in respect of addition to, or reaction with, the unsaturated linkage of the acrylonitrile or the products of acrylonitrile dimerisation. Furthermore, the solvent must not react with the phosphorus compounds or catalytic intermediates to form inactive phosphorus species at such a rate as to seriously impair the dimerisation reaction. For example, phenols have been found to be unsuitable in this respect. The organic solvent must be rigorously dried, so as not to adversely affect catalyst lifetime.

Preferably hydroxylic solvents, such as alcohols, are used, provided always that they do not react adversely with the phosphorus compound or any intermediates it may form with acrylonitrile. This may be readily established by experiment. Tertiary and secondary alcohols are preferred, for example, t-butylalcohol, 2-butanol and isopropanol. Isopropanol is often advantageous with the catalysts of the present invention in that it tends to promote faster reaction and enhance selectivity to straight-chain dimers. On the other hand, t-butanol may undergo exchange reactions with the ester groups of the phosphorus compounds to give butoxy phosphorus derivatives which evolve isobutene, thus leading to catalytically inactive phosphorus (V) species. Thus for optimum results it is advisable to determine the best solvent or solvent combination for use with the particular phosphorus (III) compound used.

The concentration of proton-donating solvent is generally in the range 0.1 to 50% by volume, calculated on the total volume of the reactants, but the optimum concentration will vary with the precise nature of the solvent and the catalyst compound. The molar concentration of proton-donating solvent will generally be greater than the molar concentration of the phosphorus (III) compound.

In order to reduce the amount of hexamer and/or other oligomers and polymers (hereafter referred to collectively as polymeric by-products or merely polymers) which may be co-produced with the desired dimeric products, it is often desirable to add a non-hydroxylic co-solvent to the reaction mixture used in our process. It will be apparent that the co-solvent must be dried to a level which maintains the overall anhydrous state of the system.

Suitable non-hydroxylic organic solvents include hydrocarbons, for example, hexane, cyclohexane, toluene, and petroleum ethers; ethers, for example, tetrahydrofuran, diethyl ether and diisopropyl ether; nitriles, for example acetonitrile, propionitrile; and fluorobenzenes. The hydrocarbon co-solvents are generally preferred.

An essential feature of the present invention is that the reaction must be conducted in the substantial absence of water. Without prejudice to our invention, we believe that the water reacts with the catalyst in the presence of acrylonitrile and/or dimeric products to give non-catalytic addition compounds. Thus, the acrylonitrile, proton-donating solvent and co-solvent must be dried before use, otherwise the catalyst lifetime may be reduced to a commercially unacceptable level. In particular acrylonitrile, which commonly contains as much as 4000 ppm of water, even after distillation, must be rigorously dried. It is also noted that phenolic stabilisers, e.g. hydroquinone and its monomethyl ether, p-methoxyphenol, which are present in acrylonitrile as supplied, should be removed, for example by treatment with activated alumina.

Any suitable drying technique may be used, provided that the final water level is sufficiently low. For example, acrylonitrile and hydroxylic solvents may be dried by being contacted with calcium hydride or a 3A or 4A molecular sieve. The above findings contrast strongly with the teachings of the prior art which makes no mention of removal of water and/or phenolic stabilisers, and in many instances advocates the addition of water and stabilisers, such as hydroquinone, to the reaction mixture. Calcium hydride is a particularly suitable drying agent, as it also reacts with phenolic stabilisers to form sparingly soluble phenates, thus effecting their removal.

Generally the concentration of acrylonitrile in the solvent or solvent mixture should range from 5 to 75% by volume. The concentration of acrylonitrile is kept as high as possible in order to optimise throughput and thus concentrations in the range 10 to 50% by volume are generally preferred.

The concentration of the phosphorus compound in the reactant mixture may be varied over a wide range, for example, from 0.005, commonly 0.01, to 5% by volume, calculated on the volume of liquid reactants; but preferably the concentration is in the range 0.01 to 1% by volume. When present, the proportion of co-solvent in the reaction mixture may be varied over wide limits. In general the ratio of proton-donating solvent to co-solvent is in the range 1/40 to 40/1; but ratios at the lower end of the range are generally preferred. However, the final choice of solvent/co-solvent ratio will depend on how it is desired to run the process and the catalyst compound used. For example, ratios in the range 1/5 to 1/20 may give rise to enhanced catalyst lifetime and increased selectivity to linear dimer, when compared with an equivalent reaction where the ratio is 1/1.

Changes in the ratio of proton-donating solvent/co-solvent are generally reflected by changes in the amount of polymers formed and changes in the reaction rate. These changes in reaction parameters are often dependent upon the actual catalyst and solvent system chosen.

The ratio of linear to branched dimers is also dependent on the solvent/co-solvent ratio in some instances. It is sometimes found that, as the proportion of proton-donating solvent decreases, the proportion of linear dimer increases, and vice-versa.

The reaction temperature is commonly in the range 0 to 180° C.; but it may be preferred to keep the range temperature below 75° C. to minimise undesirable side reactions. It is noted that the reaction will proceed below 0° C., maintaining selectivity, but at a reduced rate. In fact, in some cases improved selectivity may be obtained at lower temperatures.

The reaction may be carried out batchwise or continuously. In the latter case, it may be convenient to support the catalyst compound or to use a polymeric tervalent phosphorus compound to enable the reaction to be carried out in the liquid phase using a heterogeneous catalyst.

The dimeric products of our invention are predominantly linear $C_6$ dinitriles, especially the 1,4-dicyanobutenes. Selectivities >90 wt % (calculated on total dimeric product) may be readily obtained.

The desired products may be readily separated from the reaction mixture for example by fractional distillation or solvent extraction.

According to a further aspect of our invention, we provide the following novel compounds, which fall within the above general formulae and may be used with advantage in the process of our invention.

isopropyl bis p-isopropoxyphenylphosphinite, isopropyl phenyl(p-methoxyphenyl)phosphinite, isopropyl phenyl (p-isopropoxyphenyl)phosphinite, isopropyl phenyl (p-dimethylaminophenyl)phosphinite, isopropyl phenyl (p-tertiarybutoxyphenyl)phosphinite, di-isopropyl p-isopropoxyphenylphosphonite, di-ethyl p-isopropoxyphenylphosphonite and cyclohexyl bis p-methoxyphenylphosphinite.

The invention will be illustrated by the following Examples, in which all parts are by volume.

In all Examples, except where otherwise stated, the acrylonitrile was dried before use by means of calcium hydride. This was accomplished by adding powdered calcium hydride to the acrylonitrile overnight, then decanting the acrylonitrile on to fresh calcium hydride powder and refluxing for 150 minutes. The acrylonitrile was then distilled from the calcium hydride. Water levels were found to be in the range 30–80 ppm after this procedure. The acrylonitrile was dried finally by storing over freshly activated 3A molecular sieve to give levels below 15 ppm. Water levels were determined by the Karl Fischer titration procedure.

Isopropanol was dried as described above for ACN. Toluene was dried by refluxing it with a sodium/potassium alloy in the presence of benzophenone until the indigo colour of the ketyl was developed. The toluene was then distilled off, under an atmosphere of nitrogen, on to freshly dried 3A molecular sieve.

Cyclohexane was dried by refluxing it in the presence of triethylaluminium. The cyclohexane was then distilled off, under an atmosphere of nitrogen, on to freshly dried 3A molecular sieve.

In each case the dried solvent had a water level of <15 ppm by volume.

The phosphorus (III) compounds used in the Examples are either commercially available or were prepared using methods given in "Organo-Phosphorus Compounds" Kosolapoff and Maier published by Wiley 1972, Vol 4, Chapters 10 and 11, especially as described on pages 470 and 471.

All analyses of dimeric products were made by gas-liquid chromatography.

In all Examples, "% conversion" indicates the % by weight of acrylonitrile (ACN) converted to total dimeric, oligomeric and polymeric products; the "% yield" of a product is the weight of that product calculated as a % of the weight of ACN converted; and the "selectivity" is the proportion of straight-chain or linear dimers, calculated on the total dimeric product.

EXAMPLE 1-14

Toluene (10 parts), acrylonitrile (3 parts) isopropanol (1 part) and stated catalyst compound (0.1 part) were mixed rigorously in a glass reactor in the absence of air and moisture. The reactor vessel was then immersed in a thermostatted oil-bath for three hours. The reaction was then terminated by addition of a little water and acrylonitrile and the contents of the vessel stirred for 30 minutes. Any solid polymeric products were removed by filtration and the solvents and unreacted acrylonitrile were removed by vacuum distillation at room temperature. The non-volatile residue was analysed for dimeric products by gas-liquid chromatography (g.l.c.), the results being presented in Table 1, below. With the exception of experiment C2, in each case the phenyl substituent was in the para position.

It will be seen from the results that the use of substituted phenyl phosphorus (III) compounds gave rise to a marked increase in the rate of dimer formation, compared with the unsubstituted phenyl compounds.

| Ex No | Catalyst Compound | Temp °C | Selectivity | % Yield DCB-1 | % Solid polymers | Rel* rate |
|---|---|---|---|---|---|---|
| 1 | (MeOC$_6$H$_4$)$_2$POPr$^i$ | 60 | 89 | 70 | 3 | 100 |
| 2 | (MeOC$_6$H$_4$)$_2$POPr$^i$ | 20 | 91 | 71 | 4 | 80 |
| 3 | (Pr$^i$OC$_6$H$_4$)$_2$POPr$^i$ | 60 | 91 | 77 | 2 | 200 |
| 4 | (Pr$^i$OC$_6$H$_4$)$_2$POPr$^i$ | 20 | 93 | 79 | <1 | 25 |
| 5 | (Me$_2$NC$_6$H$_4$)$_2$POPr$^i$ | 60 | 83 | 20 | 12 | 300 |
| 6 | (Me$_2$NC$_6$H$_4$)$_2$POPr$^i$ | 20 | 85 | 30 | 8 | 250 |
| 7 | (MeC$_6$H$_4$)$_2$POPr$^i$ | 60 | 92 | 77 | <1 | 40 |
| 8 | (MeC$_6$H$_4$)$_2$POPr$^i$ | 20 | 95 | 79 | <1 | 9 |
| 9 | Ph(MeOC$_6$H$_4$)POPr$^i$ | 60 | 93 | 85 | <1 | 30 |
| 10 | Ph(MeOC$_6$H$_4$)POPr$^i$ | 20 | 97 | 60 | 1 | 10 |
| 11 | Ph(Pr$^i$OC$_6$H$_4$)POPr$^i$ | 60 | 92 | 83 | <1 | 30 |
| 12 | Ph(Pr$^i$OC$_6$H$_4$)POPr$^i$ | 20 | 95 | 70 | <1 | 8 |
| 13 | Ph(Me$_2$NC$_6$H$_4$)POPr$^i$ | 60 | 90 | 70 | 3 | 200 |
| 14 | Ph(Me$_2$NC$_6$H$_4$)POPr$^i$ | 20 | 91 | 77 | 2 | 50 |
| C2 | (o-MeOC$_6$H$_4$)$_2$POPr$^i$ | 60 | 59 | 47 | 3 | 20 |
| C1 | Ph$_2$POPr$^i$ | 60 | 95 | 85 | <1 | 1 |

"Ph" = phenyl, "Me" = methyl and Pr$^i$ = isopropyl.
C1 is a comparative test using an unsubstituted phenyl phosphorus (III) compound.
C2 is a comparative test using an orthosubstituted phenyl compound. Although the rate is enhanced relative to experiment C1, the selectivity is reduced to an unacceptable level.
*"Rel Rate" signifies the rate of acrylonitrile consumption to 25% conversion compared with that of C1 which is taken as unity.

EXAMPLES 15–25

The procedure of Examples 1–14 was followed using the phosphorus (III) compounds stated below. The reaction temperature was 60° C. in each case, with the exception of Example 25 which was conducted at 20° C. The results are given in Table 2 below. In each case the phenyl substituent was in the para position.

TABLE 2

| Ex No | Catalyst Compound | Selectivity | % Yield DCB-1 | % Solid Polymers | % Conversion |
|---|---|---|---|---|---|
| 15 | Ph(Bu$^t$OC$_6$H$_4$)POPr$^i$ | 93.0 | 77.8 | 0.1 | 33.5 |
| 16 | MeOC$_6$H$_4$P(OPr$^i$)$_2$ | 92.7 | 82.4 | 1.9 | 53.4 |
| 17 | MeOC$_6$H$_4$P(OEt)$_2$ | 93.3 | 77.3 | 2.0 | 59.4 |
| 18 | Me$_2$NC$_6$H$_4$P(OPr$^i$)$_2$ | 91.0 | 65.4 | 3.1 | 25.0 |
| 19 | Me$_2$NC$_6$H$_4$P(OEt)$_2$ | 92.1 | 57.3 | 7.8 | 88.9 |
| 20 | Pr$^i$OC$_6$H$_4$P(OPr$^i$)$_2$ | 91.8 | 68.4 | 5.8 | 50.2 |
| 21 | Pr$^i$OC$_6$H$_4$P(OEt)$_2$ | 92.9 | 82.0 | 2.2 | 49.4 |
| 22 | MeC$_6$H$_4$P(OPr$^i$)$_2$ | 93.4 | 84.5 | 1.8 | 29.5 |
| 23 | MeC$_6$H$_4$P(OMe)$_2$ | 93.8 | 76.7 | 1.7 | 30.1 |
| 24 | (MeOC$_6$H$_4$)$_2$POc.Hex | 90.7 | 86.3 | 1.2 | 59.4 |
| 25 | (MeOC$_6$H$_4$)$_2$POc.Hex | 91.6 | 81.2 | 4.2 | 28.5 |
| C2 | Ph$_2$POPr$^i$ | 96.3 | 87.2 | 0.2 | 8.1 |

*Conversion of acrylonitrile after 3 hours reaction.
"Et" = ethyl
"Bu$^t$" = tertiary butyl
"c.Hex" = cyclohexyl
C2 is a comparative test using an unsubstituted phenyl phosphorus (III) compound.

EXAMPLES 26–29

The general procedure of Examples 1–14 was repeated, but cyclohexane was used instead of toluene and reduced weight of catalyst as shown. Reaction temperature was 60° C. in each case. The results are given in Table 3 below:

TABLE 3

| Ex No | Catalyst Compound | Parts Catalyst | Selectivity | % Yield DCB-1 | % Conversion |
|---|---|---|---|---|---|
| 26 | (MeOC$_6$H$_4$)$_2$POPr$^i$ | 0.051 | 85.9 | 36.0 | 55.6 |
| 27 | Ph(MeOC$_6$H$_4$)POPr$^i$ | 0.054 | 92.5 | 59.0 | 16.2 |
| 28 | Ph(Me$_2$NC$_6$H$_4$)POPr$^i$ | 0.065 | 78.4 | 26.2 | 47.0 |
| 29 | Ph(Pr$^i$OC$_6$H$_4$)POPr$^i$ | 0.039 | 91.4 | 70.3 | 12.7 |

The phenyl substituents were in the para position.

EXAMPLES 30–31

Isopropyl phenyl (para di-ethylaminiophenyl) phosphinite was treated by the procedure of Examples 15–25 with the following results given in Table 4.

TABLE 4

| Ex No | Temp °C | Selectivity | % Yield DCB-1 | % Solid polymer | % Conversion |
|---|---|---|---|---|---|
| 30 | 20 | 91 | 74 | 5.0 | 41 |
| 31 | 60 | 88.9 | 65.3 | 4.4 | 89 |

What we claim is:

1. A process for the dimerisation of acrylonitrile to predominantly 1,4-dicyanobutenes which comprises contacting the acrylonitrile with an organic phosphorus (III) compound, the acrylonitrile being dissolved in an organic solvent capable of donating protons but substantially unreactive with acrylonitrile and the phosphorus (III) compound under the dimerisation conditions, the acrylonitrile and solvent being substantially dry, and the phosphorus (III) compound being one of formula:

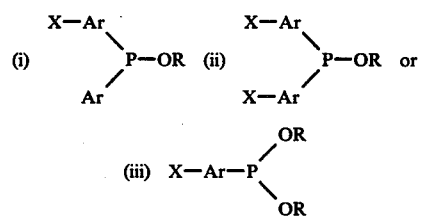

where Ar is a phenyl or naphthyl group and where groups X, which may be the same or different, are electron donating substituents of the Ar group in the para or meta positions which give rise to a negative Hammett $\sigma$ constant and R represents an alkyl or cycloalkyl group having from 1 to 8 carbon atoms, at a temperature in the range 0° to 180° C., the concentrations of acrylonitrile and said organic phosphorus (III) compound being in the range 5 to 75% and 0.01 to 5% by volume, respectively.

2. A process according to claim 1, in which the substituent X, or at least one of the substituents X, is in the para position.

3. A process according to claim 1 in which the Ar group is a phenyl group.

4. A process according to claim 1, in which the substituent X is chosen from alkoxy groups or alkylamino groups having from 1 to 8 carbon atoms.

5. A process according to claim 1, in which the phosphorus (III) compound is one of formula (ii) and the substituents X are alkyl groups.

6. A process according to claim 4 in which the phosphorus (III) compound is chosen from:
isopropyl bis p-isopropoxyphenylphosphinite, isopropyl phenyl(p-methoxyphenyl)phosphinite, isopropyl phenyl (p-isopropoxyphenyl)phosphinite, isopropyl phenyl (p-dimethylaminophenyl)phosphinite, isopropyl phenyl (p-tertiarybutoxyphenyl)phosphinite, di-isopropyl p-isopropoxyphenylphosphonite, di-ethyl p-isopropoxyphenylphosphonite, cyclohexyl bis p-methoxyphenylphosphinite, isopropyl bis p-methoxyphenylphosphinite, isopropyl bis dimethylaminophenylphosphinite, isopropyl phenyl (p-tertiarybutylphenyl)phosphinite, di-isopropyl p-methoxyphenylphosphonite, di-ethyl p-methoxyphenylphosphonite, di-isopropyl p-dimethylaminophenylphosphonite, di-ethyl p-dimethylaminophenylphosphonite, isopropyl phenyl (p-diethylaminophenyl)phosphinite.

7. A process according to claim 5, in which the phosphorus (III) compound is isopropyl bis p-methylphenylphosphinite.

8. A process according to claim 1, in which the water level of the reaction mixture is <50 ppm by volume.

9. A process according to claim 8 in which the water level of the reaction mixture is <15 ppm by volume.

* * * * *

UNITED STATES PATENT AND TRADEMARK OFFICE
CERTIFICATE OF CORRECTION

PATENT NO. : 4,138,428

DATED : February 6, 1979

INVENTOR(S) : James R. Jennings; Philip J. Hogan; Lawrence F.M. Kelly

It is certified that error appears in the above—identified patent and that said Letters Patent is hereby corrected as shown below:

IN THE HEADING

In section [30], delete "45324/76" and substitute therefore --45324/75--; delete "52888/76" and substitute therefore --52888/75--.

Signed and Sealed this

Sixteenth Day of December 1980

[SEAL]

Attest:

SIDNEY A. DIAMOND

Attesting Officer

Commissioner of Patents and Trademarks